United States Patent [19]
Lin

[11] Patent Number: 5,334,626
[45] Date of Patent: Aug. 2, 1994

[54] BONE CEMENT COMPOSITION AND METHOD OF MANUFACTURE

[75] Inventor: Steve T. Lin, Fort Wayne, Ind.

[73] Assignee: Zimmer, Inc., Warsaw, Ind.

[21] Appl. No.: 921,030

[22] Filed: Jul. 28, 1992

[51] Int. Cl.$^5$ ............ A61K 6/08; C08K 9/00; B05D 1/36
[52] U.S. Cl. .................. 523/116; 523/115; 523/207; 427/203; 427/214; 427/222
[58] Field of Search ............ 523/115, 116, 117, 206, 523/207; 427/222, 203, 214

[56] References Cited

U.S. PATENT DOCUMENTS

| | | | |
|---|---|---|---|
| 3,715,331 | 2/1973 | Molnar | 260/41 B |
| 4,404,327 | 9/1983 | Crugnola et al. | 525/228 |
| 4,456,711 | 6/1984 | Pietsch et al. | 523/206 |
| 4,500,658 | 2/1985 | Fox | 523/117 |
| 4,535,485 | 8/1985 | Ashman et al. | 623/16 |
| 4,547,390 | 10/1985 | Ashman et al. | 427/2 |
| 4,617,327 | 10/1986 | Podszun | 523/116 |
| 4,675,140 | 6/1987 | Sparks et al. | 264/4.3 |
| 4,791,150 | 12/1988 | Braden et al. | 523/117 |
| 5,061,520 | 10/1991 | Hermelin | 427/212 |

OTHER PUBLICATIONS

Literature-Howmedica-Surgical Simplex P Bone Cement-No date available.
Literature-Zimmer-Zimmer Bone Cement-Feb. 1978.
Literature-Richards-Palacos R-No date available.
Literature-Zimmer-Chemistry of Cement Settings-No date available.

Primary Examiner—Paul R. Michl
Assistant Examiner—LaVonda DeWitt
Attorney, Agent, or Firm—Cary R. Reeves

[57] ABSTRACT

A bone cement composition has adjustable rheological properties, high strength, and produces a uniform radiological image. The cement comprises beads containing a polymerization initiator in controllable concentrations from 0% to 5% or more by weight. These same beads or others may also contain an opacifier. The polymerization initiator and the opacifier may be selectively distributed throughout the beads or at specific radial locations in the beads or within the beads in specific strata. They may also be selectively placed in beads of a particular advantageous size range. Furthermore, in other embodiments of the invention, other advantageous additives can be incorporated in the beads such as dyes, antibiotics, bone growth factors, and other pharmacological or therapeutic agents.

1 Claim, 2 Drawing Sheets

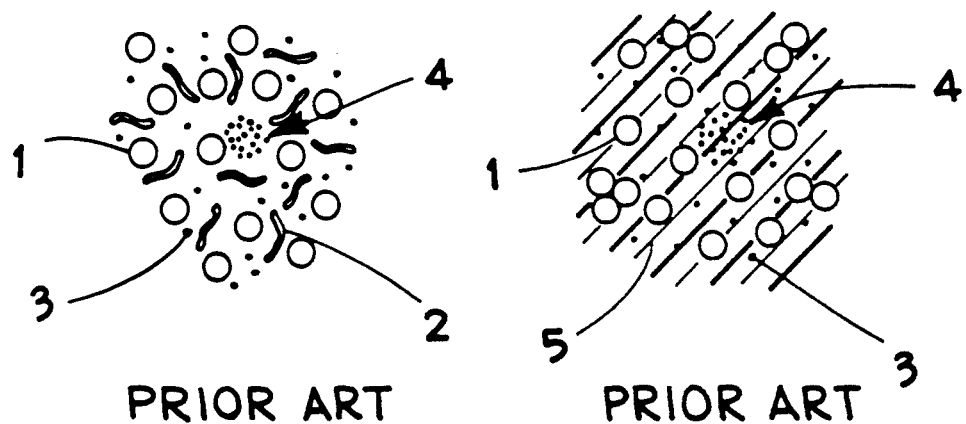
PRIOR ART
*Fig. 1*
PRIOR ART
*Fig. 3*
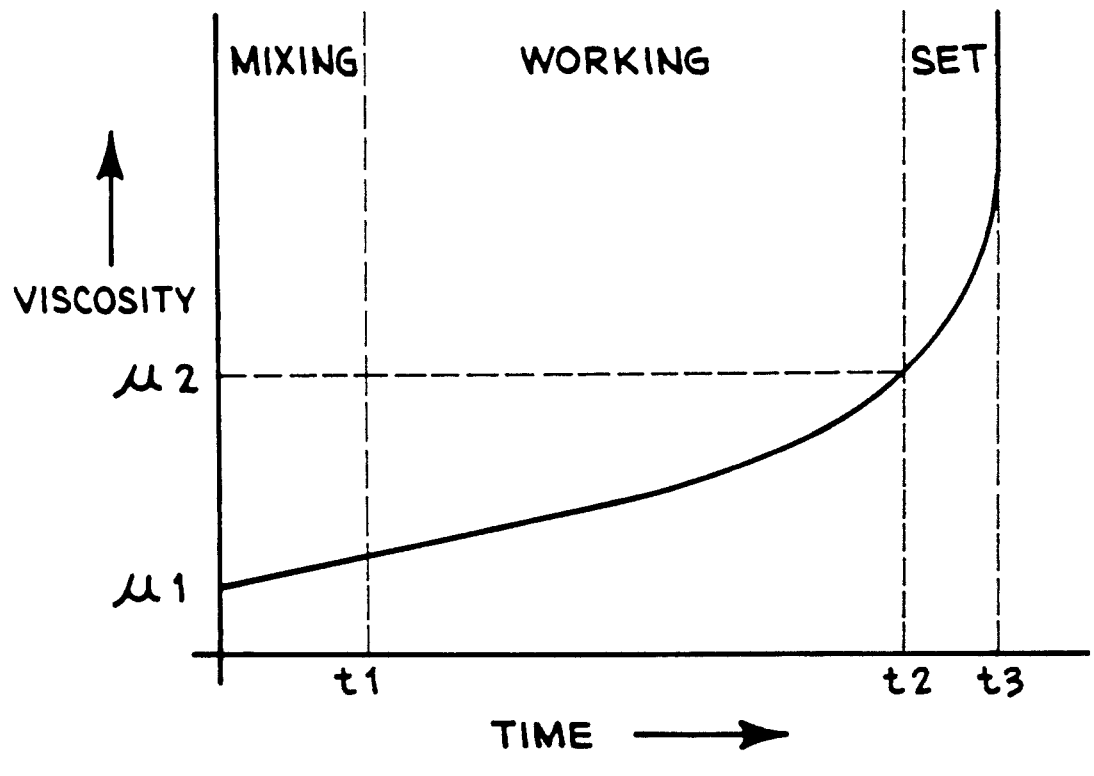
PRIOR ART
*Fig. 2*

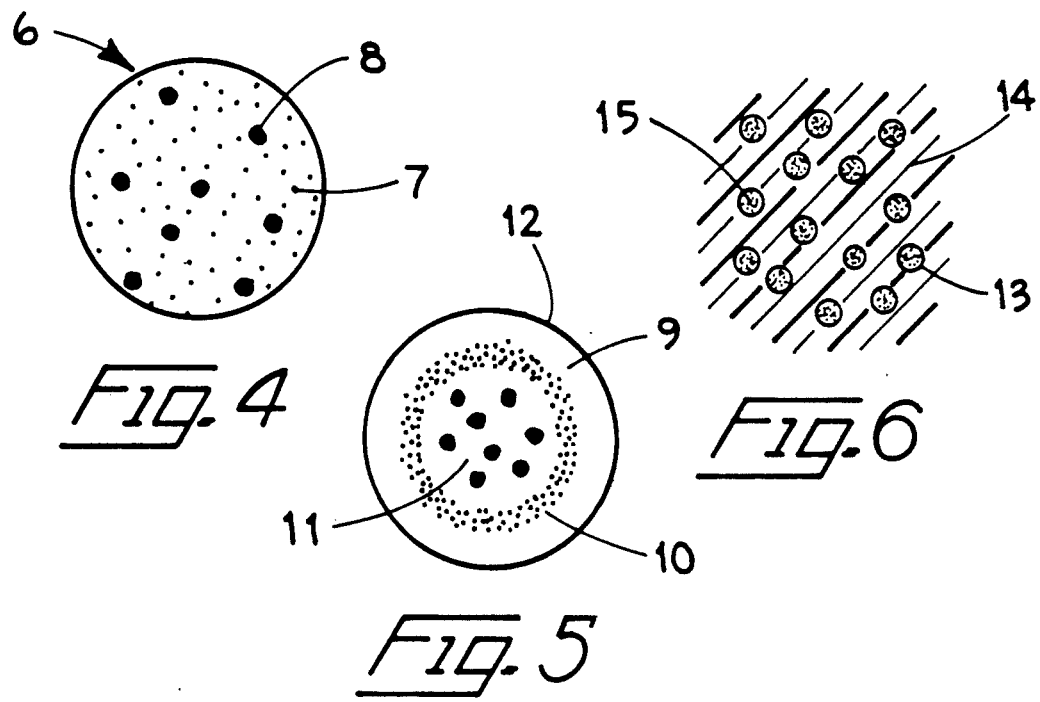
_Fig. 4_
_Fig. 5_
_Fig. 6_
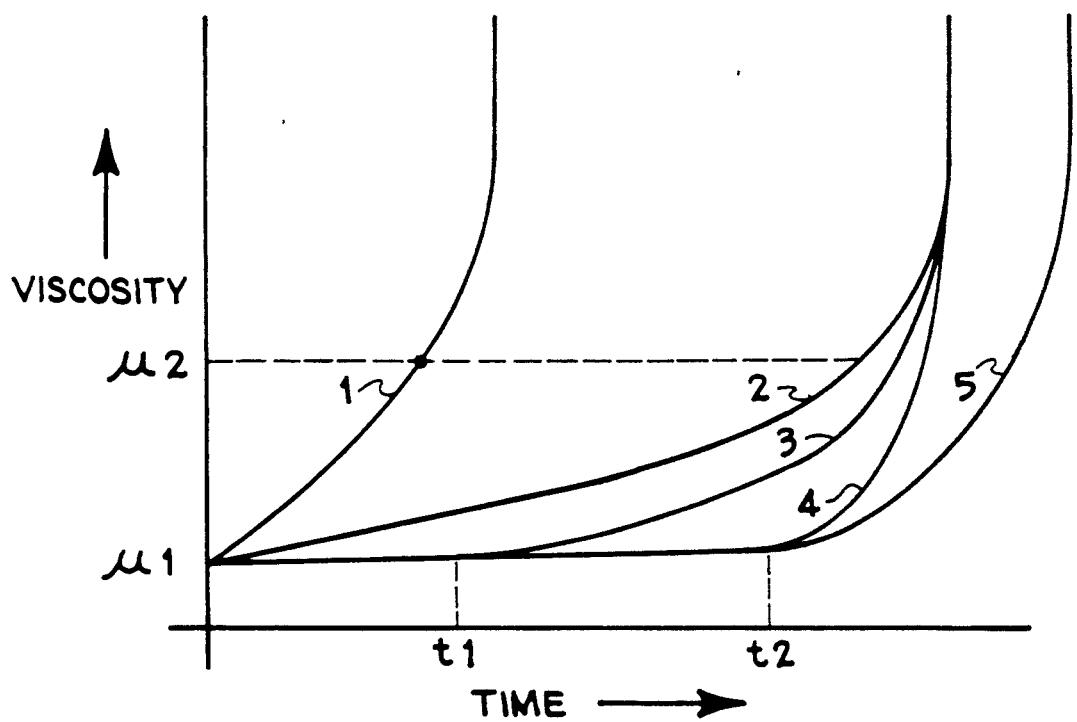
_Fig. 7_

BONE CEMENT COMPOSITION AND METHOD OF MANUFACTURE

BACKGROUND OF THE INVENTION

The present invention relates to two-component plastic systems useful for surgically filling voids in bones. More specifically, the invention relates to polymer cements comprising a liquid component and a dry component wherein the dry component includes polymer beads.

Polymer based surgical cement systems have been successfully employed for many years to fill voids in bones. Such cements have found their greatest use in the fixation of orthopaedic implants. Typically a bone is cut to accommodate an implant and then liquid and dry components of the cement system are mixed to form a paste which is applied to the cut bone. The implant is seated in this paste, which, when fully polymerized, forms a continuous solid interface between the implant and bone. The invention of this disclosure encompasses improvements in these polymer bone cements. To better understand the invention, it will be helpful to review the basic composition, behavior, and deficiencies of prior cements.

FIG. 1 depicts a typical prior art dry component of a bone cement system. The dry component includes a loose mixture of polymer beads 1, polymer flakes (or milled beads) 2, and a powdered opacifier 3. The beads contain a polymerization initiator such as benzoyl peroxide (BPO). Typically these beads are formed in a solution polymerization process in which BPO is added as a polymerization initiator to a monomer and polymerization is carried out. BPO added in excess of that required for polymerization of the monomer remains in the polymer as a residual. The more BPO added, the greater will be the residual BPO randomly distributed in the polymerized beads, within practical limits. However, the molecular weight of the resulting beads decreases as the BPO is increased. A high molecular weight is important in bone cement beads because mechanical strength increases as molecular weight increases. The tradeoff between residual BPO and molecular weight has limited the residual BPO attainable in beads having a useful molecular weight. For example, it is very difficult to produce a bead with a molecular weight greater than 500,000 and a residual BPO content greater than 2% by weight. When the residual BPO content is below approximately 1% by weight, the addition of free BPO powder to the mixture comprising the dry cement component may be required to achieve a desired set time, typically between 10 and 15 minutes. However, uniform dispersion of this BPO powder is difficult. Finally, the opacifier 3 is included to color the cement to aid its implantation and to make it visible on a radiograph. The opacifier tends to form clumps 4 because it is a fine powder added to the beads and flakes.

In use the dry component is mixed with the liquid component which contains a monomer and typically an amine accelerator such as N,N-Dimethyl-p-toluidine (DMPT). Upon mixing, the monomer dissolves the flake polymer to a great extent due to the large surface area of the flake, thereby creating a viscous fluid or paste. In addition, the monomer begins to dissolve the beads at a much slower rate than the flake because of the relatively small surface area of the beads. As the beads partially dissolve, residual BPO becomes available to the monomer. The BPO decomposes in the presence of DMPT into free radicals which act as polymerization initiators for the monomer, and polymer chains begin forming from the beads outwardly. However, only the BPO that is exposed by bead dissolution is accessible, and the beads only partially dissolve. Since the BPO is distributed throughout the bead, the usable BPO concentration of prior art cements is less than the actual concentration in the bead. As polymerization progresses, the cement paste grows more viscous until it eventually hardens into a solid. It is helpful to characterize this hardening process as having three stages. FIG. 2 depicts a viscosity versus time graph for a typical polymer bone cement. During the first, or mixing stage, the cement components are mixed and a viscous paste, represented by $\mu_1$, is formed primarily due to the dissolution of the polymer flake in the monomer. During the second stage, or working time, the paste is of a suitable viscosity to be effectively applied to the bone. By design this may be a fairly thick putty-like consistency suitable for manually packing into the bone or it may be a thinner flowable consistency suitable for injection into the bone. The consistency can by controlled, for example, by varying the ratio of flake to beads in the dry component. It is noted that absent the BPO this stage would continue for a considerable period with only slight thickening due to further dissolution of the beads. However, because of the BPO, polymerization takes place and the paste reaches a state, represented by $\mu_2$, where it is no longer able to be worked. The polymerization reaction, which is exothermic, continues during the final stage until the cement is fully hardened. The entire process typically takes from two to fifteen minutes. Because of the practical limits on the amount of residual BPO and its distribution throughout the beads, the viscosity versus time curve, as shown in FIG. 2, for prior art cements is not readily tailored.

The resulting solid cement, as depicted in FIG. 3, comprises a matrix of polymerized plastic 5 containing a distribution of beads 1 and opacifier 3. The beads are generally firmly attached to the matrix since the polymer chains formed from the beads outwardly as BPO was exposed. However, if free BPO was added to raise BPO levels, then when the dry cement component having a non-uniform dispersion of BPO powder is mixed with the liquid cement component, polymerization will proceed more quickly at regions of relatively high BPO concentration. These regions will be outside of the beads, resulting in localized and less uniform polymerization which can result in reduced mechanical properties. Furthermore, the opacifier is simply encased in the matrix and forms no attachment with it, thereby concentrating stresses placed on the cement and weakening it. The tendency of the opacifier to clump 4 can further weaken the cement and the clumps can obscure the radiographic image of the cement-bone interface. U.S. Pat. Nos. 4,791,150 to Braden et al. and 4,500,658 to Fox describe cements having an opacifier dispersed in polymer cement beads during the bead formation. The references teach the use of a suspension polymerization batch process for forming beads as discussed above and further teach including the opacifier particles in the suspension polymerization solution so that the beads formed will contain some opacifier. This method of incorporating opacifier is tedious and costly to use. It also produces a bead with an uncontrolled and random opacifier distribution. As a result some of the opacifier particles will likely by located near the bead surface, allowing the particles to become exposed and separated from the bead when the surface is dissolved by the monomer during use. Such separated particles will be deposited in the matrix and can form stress concentrators as previously described.

SUMMARY OF THE INVENTION

It is therefore an object of the present invention to provide a polymeric bone cement composition having a particularly useful viscosity versus time curve.

It is also an object of the present invention to provide a polymeric bone cement composition having improved strength due to the reduction of stress concentrating structures in the polymerized cement.

It is a further object of the present invention to provide a polymeric bone cement composition having a uniform radiographic image.

It is also an object of the present invention to provide a polymeric bone cement with advantageous additives strategically placed in controlled distributions within the cement dry component beads.

It is also an object of the present invention to provide a polymeric bone cement having beneficial additives strategically placed in particular advantageously sized cement dry component beads.

It is a still further object of the present invention to provide a method of manufacturing a polymeric bone cement composition that enables the cement's viscosity versus time curve to be readily adjusted.

It is finally an object of the present invention to provide a method of manufacturing a polymeric bone cement composition that provides for the placement of the opacifier and other additives in controlled distributions in the cement.

The above advantageous objects and others are obtained by a cement composition comprising beads containing a polymerization initiator in controllable concentrations from 0% to 5% or more by weight. These same beads or others may also contain an opacifier. The polymerization initiator and the opacifier may be selectively distributed throughout the beads or at specific radial locations in the beads or within the beads in specific strata. They may also be selectively placed in beads of a particular advantageous size range. Furthermore, in other embodiments of the invention, other advantageous additives can be incorporated in the beads such as dyes, antibiotics, bone growth factors, and other pharmacological or therapeutic agents. Beads having the above described structure can be formed using a modified form of the microencapsulation technique described in U.S. Pat. No. 4,657,140 hereby incorporated by reference.

BRIEF DESCRIPTION OF THE DRAWINGS

The before mentioned features and advantages of the present invention are apparent from the following detailed description and the drawings wherein:

FIG. 1 is a schematic diagram of a prior art dry component of a polymeric cement system.

FIG. 2 is a viscosity versus time graph for a typical prior art polymeric cement system.

FIG. 3 is a schematic diagram of a prior art polymeric cement system having been fully polymerized.

FIG. 4 is a schematic diagram of a cement bead with additives distributed within it.

FIG. 5 is a schematic diagram of a cement bead with additives distributed in layers.

FIG. 6 is a schematic diagram of the inventive polymeric cement system having been fully polymerized.

FIG. 7 is a graph of several viscosity versus time curves achievable by the present inventive bone cements.

DETAILED DESCRIPTION OF THE INVENTION

Referring to FIG. 4 a polymer bead 6 has one or more additives distributed within it. A polymerization initiator 7, preferably benzoyl peroxide (BPO), may comprise from 0% to 5% or more of the bead weight. Such beads can be combined with other beads of different sizes and compositions to form the dry component of a surgical cement system. Controlled, variable BPO concentrations, made by the bead forming process described hereinbelow, contribute to adjustable rheological behavior in the cement system. The bead 6, or another, preferably includes an opacifier 8, such as barium sulphate ($BaSO_4$). By encasing the $BaSO_4$ in the spherical and relatively strong bead, it is prevented from forming a stress concentrator in the polymerized cement matrix and it will produce a uniform radiographic image. Furthermore, the $BaSO_4$ is preferably incorporated in beads having a size, or maximum dimension, larger than can be dissolved during the working stage so that the $BaSO_4$ is less likely to be freed from the beads and deposited in the polymerizing matrix. An exemplary cement dry component would contain 85% by weight beads containing $BaSO_4$ and BPO, the beads having an average size of approximately 50 $\mu$m. The $BaSO_4$ would be in the form of a fine powder comprising particles approximately 1 $\mu$m in size and constituting approximately 8%–12% of the bead weight. The $BaSO_4$ is depicted as forming clumps 8 within the bead 6. The BPO would be in the form of a fine powder comprising particles 7 approximately 10 $\mu$m in size and constituting 2%–3% of the bead weight. The remaining 15% by weight of the cement dry component would consist of fine polymer beads having an approximate average size of 1 $\mu$m to 10 $\mu$m. This portion of the dry component could also comprise milled beads or flaked polymer. An alternate exemplary cement dry component would contain 75% by weight beads containing BPO, 10% by weight beads containing $BaSO_4$ and 15% by weight fine beads, milled beads or flake. Additionally, BPO can be placed in the fine beads so that it is all available rapidly upon dissolution of the fine beads.

The placement of additives in beads can be even more advantageously effected by placing the additives in strata or layers. FIG. 5 depicts a bead having layers 9, 10 and 11 and surface 12. By placing the opacifier in the center 11 of the bead, it is well imbedded and there is little chance of it being loosely incorporated into the matrix of the polymerized cement. The polymerization initiator can be placed on the surface 12 of the bead in order to cause polymerization to begin immediately upon mixing of the dry and liquid cement components. It can also be placed within the outer layer of the bead to cause more gradual polymerization as it is made available due to dissolution of the bead. Finally, the initiator can be placed in a layer 10 deeper into the bead with a polymer barrier layer 9 surrounding the initiator containing layer to provide a cement with a specific time delay before polymerization begins. This time delay would be the time required for the barrier layer 9 to dissolve and expose the polymerization initiator containing layer 10. Furthermore the initiator can be concentrated in narrow bands in order to produce a time delay until the band is reached and then very rapid polymerization, or the bands can be less concentrated or wider to provide a time delay with a more gradual polymerization onset. The novel banding of the invention would enable full utilization of all of the BPO contained in the beads since the BPO would be placed in the regions of the bead that will be exposed in use. Such strategic incorporation of additives can yield specific, desirable rheological behavior and strength characteristics, Likewise, the above structure can advantageously accommodate other additives such as dyes, antibiotics, bone growth factors, and other useful agents.

According to the present invention the additives can be placed in beads of specific sizes, they can be placed singly or in combination with other additives, and they can advantageously be placed in strata to achieve precise timing and positive encapsulation. All of the above structures can be produced by modifying the process described in U.S. Pat. No. 4,657,140. In this process solid particles or viscous liquid droplets of core material are encapsulated in a coating material by feeding a suspension or solution of the two materials onto a rotating surface. This process is distinguished from other processes used to form bone cement beads containing additives in that it is a continuous process and it is capable of forming beads having a wide range of controlled sizes. Coated particles and droplets of excess coating material are centrifugally thrown from the perimeter of the rotating surface and solidified by cooling or evaporation. The excess coating material forms dried droplets smaller than the coated particles and can therefore be easily separated and recycled. The continuous and controllable nature of the process and the ease of separating product from recyclable coating material makes the process more economical and more efficient than other processes. It also makes the process applicable where it is desirable to have only coated particles in the final product. This process is capable of coating particles ranging from 1 $\mu$m to 500 $\mu$m and can produce finished beads in a variety of specific sizes as needed. In the instant invention, a bead as shown in FIG. 4 can be made by the above process by liquefying a polymer, such as by dissolving it in a solvent or melting it, and suspending or dissolving the desired additive or additives in the liquid and then feeding the suspension or solution to the rotating surface. In the preferred embodiment, bulk polymethylmethacrylate (PMMA) homopolymer or polymethylmethacrylate styrene (PMMAS) co-polymer with no or minimal residual BPO, and a molecular weight of at least 100,000 is dissolved in an organic solvent such as acetone, methylene chloride, or other known organic solvents. BPO, typically in the form of a fine powder, is dissolved (or suspended depending on the solvent used) in the polymer solution. Since the beads are formed directly from a polymer rather than in a polymerization reaction, any desirable BPO concentration can be achieved without affecting the attainable molecular weights. In addition to BPO, BaSO$_4$ with an average particle size of 1 micrometer or less is preferably co-suspended in the solution. The suspension is fed to the rotating atomization equipment where centrifugal force causes the suspension to atomize when it leaves the rotating surface. The pure polymer beads formed from excess coating material can be recycled or incorporated as fine beads into the dry component of the cement system to provide desired properties. The process can also be run without any additives to produce only pure polymer beads for incorporation into the dry component. Other additives that can be advantageously placed in beads include dyes, antibiotics, bone growth factors, and other pharmacological or therapeutic agents. This process is particularly suited to incorporating fragile pharmacological agents because of the potential for a very short dwell time of the additive in solution and the ability to conduct the process at low temperatures.

A layered bead as shown in FIG. 5 can be produced by iteratively using the beads from a prior coating step as the particles in subsequent coating steps. For example, a bead having BaSO$_4$ encapsulated at its center surrounded by a layer of concentrated BPO and an outer layer of pure PMMA can be produced by the following steps. The above process is employed to produce first beads having BaSO$_4$ encapsulated in PMMA. These first beads are then suspended in a solution containing BPO, such as BPO dissolved in methanol. (The first beads are not soluble in methanol. However, it is even possible to use the process for particles or beads soluble in the solution since dwell time can be made to be so short as to prevent dissolution of the particles.) The process is carried out to yield second beads comprising BaSO$_4$ encapsulated in PMMA, the second beads being coated with BPO. The process is repeated with a PMMA solution to apply the final PMMA outer layer. A wider, less concentrated, BPO containing layer could be produced by coating the first beads with a more viscous liquid containing BPO, such as liquified polymer, rather than BPO dissolved in methanol. A cement system having a dry component comprising these beads in an appropriate mix with fine beads, milled beads, or polymer flake will have the highly desirable properties of a controlled specific working time (time to dissolve through outer layer of PMMA) followed by onset of rapid polymerization as the concentrated layer of BPO becomes available. FIG. 6 depicts the fully polymerized cement. The beads 13 will be securely incorporated in the polymer matrix 14 since polymerization initiates from the beads. The BaSO$_4$ 15 will be securely held in the bead centers where it cannot weaken the cement and where it will be uniformly distributed with the beads throughout the hardened cement to yield a uniform radiographic image.

The present invention provides for careful tailoring of the rheological properties of bone cements and for improvement in the strength of bone cements. FIG. 7 depicts several exemplary viscosity versus time curves obtainable by the inventive cements described herein. These curves range from immediate, rapid polymerization to delayed progressive polymerization. For example, curve 1 represents a cement that begins to polymerize immediately and continues to harden very rapidly. This type of curve would result from a cement having a high concentration of a polymerization initiator in small readily dissolved beads whereby the polymerization initiator would all be released by dissolution of the beads during mixing. Curve 2 represents a cement that begins to polymerize during mixing and continues to polymerize at a gradually increasing rate. This curve would result from a bead having a polymerization initiator dispersed throughout the bead so that some polymerization initiator is exposed immediately and as more of the bead dissolves, more polymerization initiator becomes available. Curve 3 represents a cement having a delay t$_1$ before polymerization begins and then continued polymerization at a gradually increasing rate. This curve would result from a layered bead having an outer layer containing no polymerization initiator and a relatively wide, or less concentrated, inner layer containing polymerization initiator so that once the outer layer is dissolved, the polymerization initiator is gradually released. Curve 4 represents a cement having a relatively long delay $t_2$ before polymerization begins and then rapid polymerization. This curve would result from a layered bead structure having a thick outer layer with no polymerization initiator and then a very concentrated band of polymerization initiator which is released quickly. Finally curve 5 represents a cement having a long delay and gradual polymerization. This would result from a layered bead structure having a thick outer layer with no polymerization initiator and a wide inner layer that would gradually release polymerization initiator. Many other desirable polymerization curves could be obtained using the techniques of this invention.

While the foregoing has described exemplary embodiments of the present invention, further variations are possible. For example, bead sizes may vary depending on the particular additive employed and its source. Likewise, the order, thickness, and concentration of layers in a layered bead structure will be varied to suit a particular application and produce desired properties. In addition, the cement may comprise a polymer or combination of polymers different from those used in the examples. However, it will be understood by those skilled in the art that these modifications and others may be made without departing from the spirit and scope of the invention defined by the appended claims.

What is claimed is:

1. A method of manufacturing beads for incorporation into the dry component of a bone cement comprising the steps of:
    (a) forming a first opacifier containing bead by solidifying a first liquid comprising a liquified polymer combined with an opacifier;
    (b) coating the first bead to form a second, layered bead by coating the first bead with a second liquid comprising a liquified polymer combined with a polymerization initiator and solidifying the coating.

* * * * *